(12) United States Patent
Orbay

(10) Patent No.: US 6,364,882 B1
(45) Date of Patent: Apr. 2, 2002

(54) VOLAR FIXATION SYSTEM

(75) Inventor: Jorge L. Orbay, Miami, FL (US)

(73) Assignee: Hand Innovations, Inc., Miami, FL (US)

( * ) Notice: Subject to any disclaimer, the term of this patent is extended or adjusted under 35 U.S.C. 154(b) by 0 days.

(21) Appl. No.: 09/524,058

(22) Filed: Mar. 13, 2000

Related U.S. Application Data

(63) Continuation-in-part of application No. 09/495,854, filed on Feb. 1, 2000.

(51) Int. Cl.$^7$ .............................................. A61B 17/80
(52) U.S. Cl. ........................................ 606/69; 606/60
(58) Field of Search ............................ 606/72, 60, 69, 606/70, 71; 623/21.12

(56) References Cited

U.S. PATENT DOCUMENTS

| | | | | | |
|---|---|---|---|---|---|
| 2,500,370 | A | * | 3/1950 | McKibbin | 606/47 |
| 3,741,205 | A | * | 6/1973 | Markolf et al. | 606/61 |
| 4,867,144 | A | | 9/1989 | Karas | 128/92 YF |
| 5,015,248 | A | * | 5/1991 | Burstein et al. | 606/74 |
| 5,304,180 | A | * | 4/1994 | Slocum | 606/69 |
| 5,437,667 | A | * | 8/1995 | Papierski et al. | 606/55 |
| 5,531,745 | A | | 7/1996 | Ray | 606/61 |
| 5,853,413 | A | | 12/1998 | Carter et al. | 606/69 |
| 5,968,047 | A | | 10/1999 | Reed | 606/76 |
| 6,096,040 | A | * | 8/2000 | Esser | 606/69 |
| 6,183,475 | B1 | * | 2/2001 | Lester et al. | 606/69 |
| 6,197,028 | B1 | * | 3/2001 | Ray et al. | 606/61 |
| 6,221,073 | B1 | * | 4/2001 | Weiss et al. | 606/60 |
| 6,283,969 | B1 | * | 9/2001 | Grusin et al. | 606/69 |

* cited by examiner

*Primary Examiner*—Jeffrey A. Smith
*Assistant Examiner*—Michael B. Priddy
(74) *Attorney, Agent, or Firm*—David P. Gordon; David S. Jacobson; Thomas A. Gallagher

(57) ABSTRACT

A volar fixation system includes a T-shaped plate intended to be positioned against the volar side of the radial bone, a plurality of bone screws for securing the plate along an non-fractured portion of the radial bone, and a plurality of bone pegs which extend from the plate and into bone fragments of a Colles' fracture. The plate is a T-shaped plate including a plurality of screw holes and a plurality of threaded peg holes. According to a first preferred aspect of the invention, the peg holes are preferably linearly or parabolically arranged and provided such that the holes are positioned increasingly distal in a medial to lateral direction along the second side. According to a second preferred aspect, axes through the holes are oblique relative to each other and preferably angled relative to each other in two dimensions. The system includes a guide plate which temporarily sits on top of the volar plate and includes holes oriented according to the axes of the peg holes for guiding a drill into the bone fragments at the required orientation. The volar plate is positioned against the radius and screws are inserted through the screw holes to secure the volar plate to the radius. The bone fragments are aligned, and the guide plate assists in drilling pilot hole. The pegs are inserted through the peg holes and into the drilled holes in the bone. The volar system thereby secures the bone fragments in proper orientation.

35 Claims, 5 Drawing Sheets

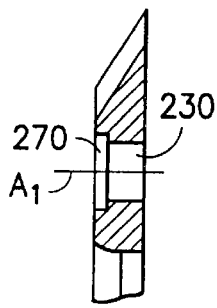 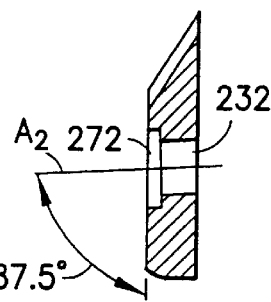 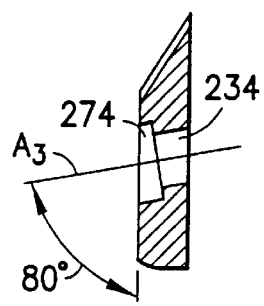 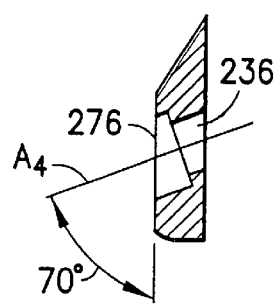
FIG.16  FIG.17  FIG.18  FIG.19
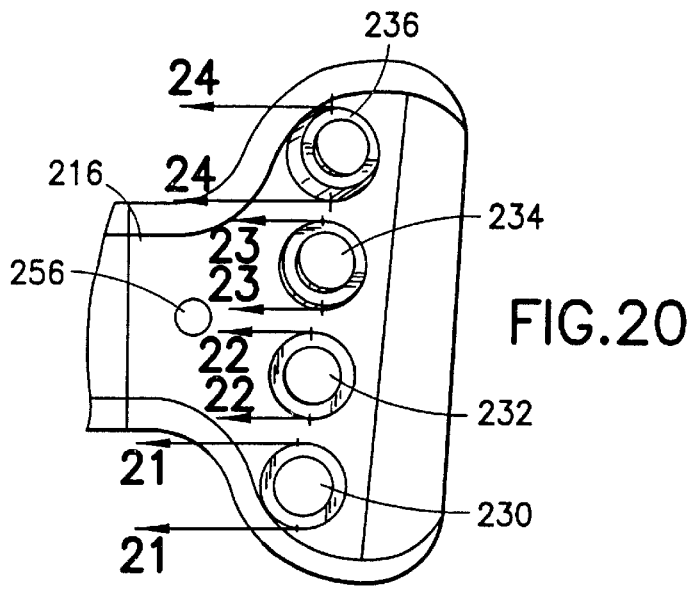
FIG.20
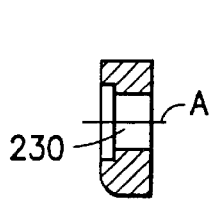 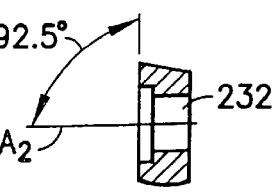 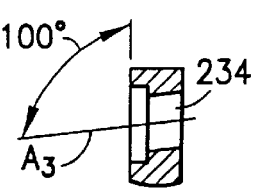 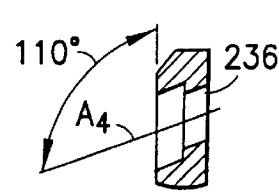
FIG.21  FIG.22  FIG.23  FIG.24

VOLAR FIXATION SYSTEM

This application is a continuation-in-part of U.S. Ser. No. 09/495,854, filed Feb. 1, 2000, which is hereby incorporated by reference herein in its entirety.

BACKGROUND OF THE INVENTION

1. Field of the Invention

This invention relates broadly to surgical devices. More particularly, this invention relates to a bone fixation system, and particularly to a fixation system adapted to fixate a Colles' (or distal radial) fracture.

2. State of the Art

Referring to FIG. 1, a Colles' fracture is a fracture resulting from compressive forces being placed on the distal radius 10, and which causes backward displacement of the distal fragment 12 and radial deviation of the hand at the wrist 14. Often, a Colles' fracture will result in multiple bone fragments 16, 18, 20 which are movable and out of alignment relative to each other. If not properly treated, such fractures result in permanent wrist deformity. It is therefore important to align the fracture and fixate the bones relative to each other so that proper healing may occur.

Alignment and fixation are typically performed by one of several methods: casting, external fixation, interosseous wiring, and plating. Casting is non-invasive, but may not be able to maintain alignment of the fracture where many bone fragments exist. Therefore, as an alternative, external fixators may be used. External fixators utilize a method known as ligamentotaxis, which provides distraction forces across the joint and permits the fracture to be aligned based upon the tension placed on the surrounding ligaments. However, while external fixators can maintain the position of the wrist bones, it may nevertheless be difficult in certain fractures to first provide the bones in proper alignment. In addition, external fixators are often not suitable for fractures resulting in multiple bone fragments. Interosseous wiring is an invasive procedure whereby screws are positioned into the various fragments and the screws are then wired together as bracing. This is a difficult and time consuming procedure. Moreover, unless the bracing is quite complex, the fracture may not be properly stabilized. Plating utilizes a stabilizing metal plate typically against the dorsal side of the bones, and a set of parallel pins extending from the plate into the holes drilled in the bone fragments to provide stabilized fixation of the fragments. However, the currently available plate systems fail to provide desirable alignment and stabilization.

SUMMARY OF THE INVENTION

It is therefore an object of the invention to provide an improved fixation and alignment system for a Colles' fracture.

It is another object of the invention to provide a volar fixation system which desirably aligns and stabilizes multiple bone fragments in a distal radial fracture to permit proper healing.

In accord with these objects, which will be discussed in detail below, a volar fixation system is provided which generally includes a T-shaped plate intended to be positioned against the volar side of the radial bone, a plurality of bone screws for securing the plate along a non-fractured portion of the radial bone, and a plurality of bone pegs which extend from the plate and into bone fragments of a Colles' fracture.

The plate is generally a T-shaped plate defining an elongate body, a head portion angled relative to the body, a first side which is intended to contact the bone, and a second side opposite the first side. The body portion includes a plurality of countersunk screw holes for the extension of the bone screws therethrough. The head portion includes a plurality of threaded peg holes for receiving the pegs therethrough. According to a first embodiment, the peg holes are preferably non-linearly arranged. According to a second embodiment, the peg holes are preferably linearly arranged. In either embodiment, the peg holes are positioned increasingly distal in a medial to lateral direction along the second side. According to a preferred aspect of the invention, axes through the holes are oblique relative to each other, and are preferably angled relative to each other in two dimensions. The pegs having a threaded head and a relatively smooth cylindrical shaft.

The system preferably also includes a guide plate which temporarily sits on top of the volar plate and includes holes oriented according to the axes of the peg holes for guiding a drill into the bone fragments at the required orientation. The volar plate and guide plate are also preferably provided with mating elements to temporarily stabilize the guide plate on the volar plate during the hole drilling process.

In use, the volar plate is positioned with its first side against the volar side of the radius and bone screws are inserted through the bone screw holes into the radius to secure the volar plate to the radius. The bone fragments are then aligned and the guide plate is positioned on the second side of the volar plate. A drill, guided by guide holes in the guide plate, drills holes into the bone fragments, and the guide plate is then removed.

The pegs are then inserted through the peg holes and into the holes in the bone, and the heads of the pegs are threadably engaged in the volar plate. The volar fixation system thereby secures the bone fragments in their proper orientation.

Additional objects and advantages of the invention will become apparent to those skilled in the art upon reference to the detailed description taken in conjunction with the provided figures.

BRIEF DESCRIPTION OF THE DRAWINGS

FIGS. 16–19 are section views across line 16—16, 17—17, 18—18, and 19—19, respectively in FIG. 15;

FIG. 20 is second partial top view of the head portion of the left hand volar plate according to the second embodiment of the volar fixation system of the invention; and FIGS. 21–24 are section views across line 21—21, 22—22, 23—23, and 24—24, respectively in FIG. 20.

DETAILED DESCRIPTION OF THE PREFERRED EMBODIMENTS

Figure 1:
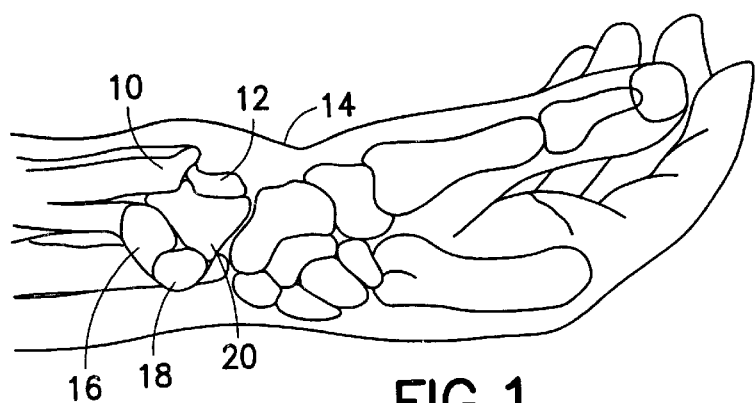
FIG. 1 is an illustration of an extremity subject to a Colles' fracture.
Figure 2:
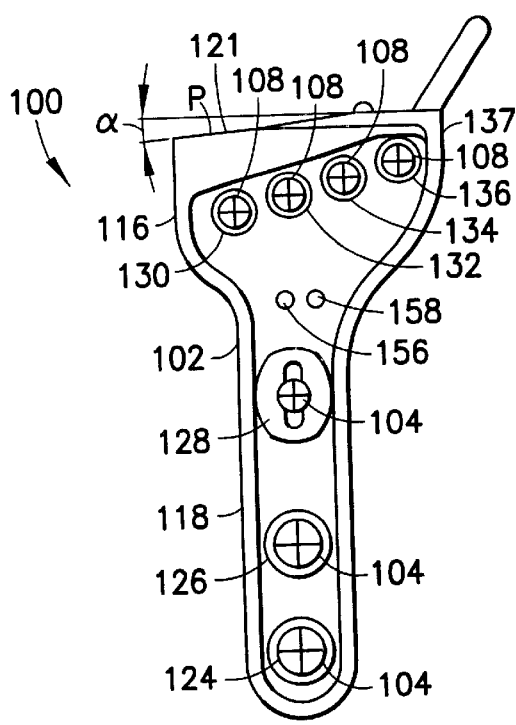
FIG. 2 is a top volar view of a right hand volar fixation system according to a first embodiment of the invention.
Figure 3:
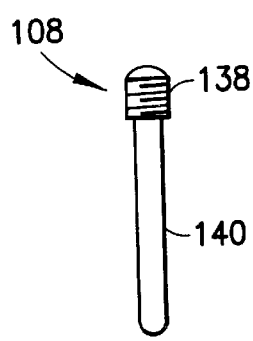
FIG. 3 is a side view of a bone peg according to the first embodiment of the volar fixation system of the invention.
Figure 4:
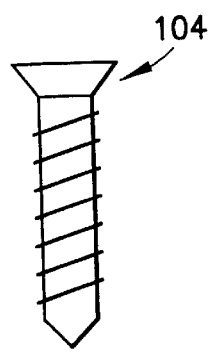
FIG. 4 is a side view of a bone screw of the volar fixation system of the invention.

Turning now to FIGS. 2 through 4, a first embodiment of a volar fixation system 100 for aligning and stabilizing multiple bone fragments in a Colles' fracture generally includes a substantially rigid T-shaped plate 102 intended to be positioned against the volar side of the radial bone, a plurality of preferably self-tapping bone screws 104 for securing the plate 102 along a non-fractured portion of the radial bone, and a plurality of bone pegs 108 which extend from the plate 102 and into bone fragments of a Colles' fracture.

Figure 5:
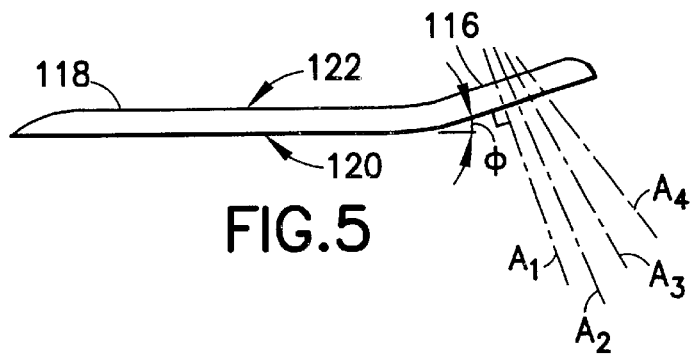
FIG. 5 is a side view of the right hand volar plate of the volar fixation system according to the first embodiment of the invention.
Figure 6:
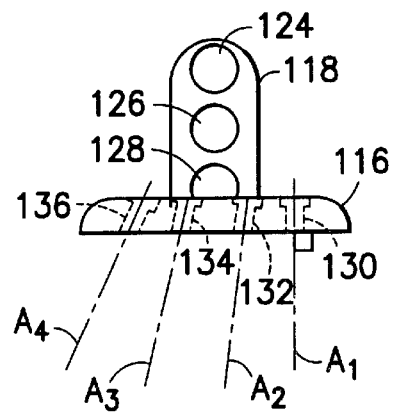
FIG. 6 is a front end view of the right hand volar plate of the volar fixation system according to the first embodiment of the invention.

Referring to FIGS. 2, 5 and 6, more particularly, the T-shaped plate 102 defines a head portion 116, an elongate body portion 118 angled relative to the head portion, a first side 120 which is intended to contact the bone, and a second side 122 opposite the first side. The first side 120 at the head portion is preferably planar, as is the first side at the body portion. As the head portion and body portion are angled relative to each other, the first side preferably defines two planar portions. The angle Φ between the head portion 116 and the body portion 118 is preferably approximately 18° and bent at a radius of approximately 1.00 inch (FIG. 5). The distal edge 121 of the head portion 116 is preferably angled proximally toward the medial side at an angle α, e.g., 5°, relative to a line P, which is perpendicular to the body portion. The head portion 116 preferably has a width of 0.913 inch and a greatest proximal-distal dimension (i.e., from the corner of angle a to the body portion) of approximately 0.69 inch, and the body portion preferably has a width of 0.375 inch and a length of 1.40 inches. The plate 102 preferably has a thickness of approximately 0.098 inch. The plate 102 is preferably made from a titanium alloy, such as Ti-6A-4V.

The body portion 118 includes three preferably countersunk screw holes 124, 126, 128 for the extension of the bone screws 104 therethrough. The first screw hole 124 has a center preferably 0.235 inch from the end of the body portion, the second screw hole 126 has a center preferably 0.630 inch from the end of the body portion, and the third screw hole 128 is preferably generally elliptical (or oval) and defines foci-like locations at 1.020 inches and 1.050 inches from the end of the body portion. The head portion 116 includes four threaded peg holes 130, 132, 134, 136 for individually receiving the pegs 108 therethrough. According to a first preferred aspect of the first embodiment of the invention, the peg holes 130, 132, 134, 136, preferably 0.100 inch in diameter, are preferably non-linearly arranged along the head portion 116, and are provided such that the adjacent peg holes are provided further distally in a medial to lateral direction along the second side. More particularly, according to a preferred aspect of the first embodiment of the invention, the peg holes are preferably arranged along a parabolic curve, with the center of peg hole 130 located approximately 0.321 inch proximal line P and approximately 0.719 inch medial of the lateral edge 137 of the head portion, the center of peg hole 132 located approximately 0.296 inch proximal line P and approximately 0.544 inch medial of the lateral edge 137, the center of peg hole 134 located approximately 0.250 inch proximal line P and approximately 0.369 inch medial of the lateral edge 137, and the center of peg hole 136 located approximately 0.191 inch proximal line P and approximately 0.194 inch medial of the lateral edge 137.

In addition, according to a second preferred aspect of the first embodiment of the invention, the peg holes define axes $A_1$, $A_2$, $A_3$, $A_4$ which are oblique (not parallel) relative to each other, and more preferably are angled in two dimensions (medial/lateral and proximal/distal) relative to each other; i.e., the pegs once inserted into the peg holes are also angled in two dimensions relative to each other. More particularly, the first axis $A_1$ of the first peg hole 130 (that is, the most proximal and medial peg hole) is preferably directed normal to the first side 120 of the head portion 116. The axis $A_2$ of the adjacent peg hole 132, i.e., the second axis, is preferably angled approximately 1–7° distal and lateral relative to the first axis $A_1$, and more preferably approximately 2.5° distal and lateral relative to the first axis $A_1$. The axis $A_3$ of the peg hole 134 laterally adjacent the second peg hole 132, i.e., the third axis, is preferably angled approximately 7–13° distal and lateral relative to the first axis $A_1$, and more preferably approximately 10° distal and lateral relative to the first axis $A_1$. The axis $A_4$ of the peg hole 134 laterally adjacent the third peg hole 132, i.e., the fourth axis, is preferably angled approximately 10–30° distal and lateral relative to the first axis $A_1$, and more preferably approximately 20° distal and lateral relative to the first axis $A_1$. The second side of the head portion 116, distal of the peg holes 130, 132, 134, 136 is preferably beveled.

Referring back to FIG. 3, the pegs 108, preferably approximately 0.872 inch in length, each have a threaded head 138 adapted to threadably engage the threads about the peg holes 130, 132, 134, 136, and have a relatively smooth non-threaded cylindrical shaft 140. The shafts 140 are preferably approximately 0.0675 inch in diameter and 0.765 inch in length. Such dimensions permit the pegs to adequately support the bone fragments such that the bone is able to heal correctly. The pegs 108 are also preferably made from titanium alloy, and may be coated in a ceramic, e.g., titanium nitride, to provide a bone interface which will not adversely affect bone healing.

Figure 7:
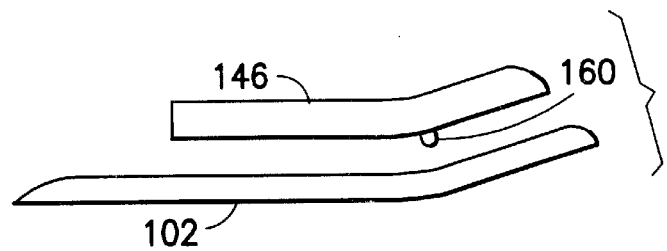
FIG. 7 is an exploded side view of the right hand volar plate and guide plate according to the first embodiment of the fixation system of the invention.
Figure 8:
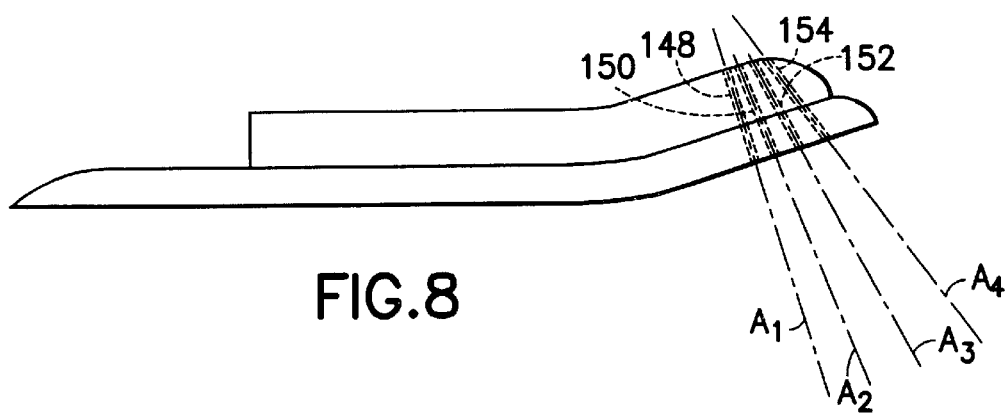
FIG. 8 is a side view of the guide plate positioned on the right hand volar plate to provide drill guide paths in accord with the invention.
Figure 9:
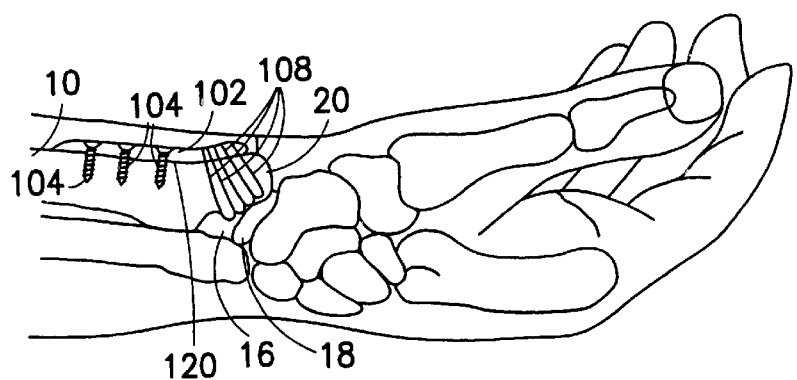
FIG. 9 is an illustration of the first embodiment of the volar fixation system provided in situ aligning and stabilizing a Colles' fracture.

Turning now to FIGS. 7 and 8, the system 100 preferably also includes a guide plate 146 which temporarily sits on the second side 122 of the volar plate 102 and includes guide holes 148, 150, 152, 154 (illustrated in overlapping section in FIG. 8) oriented according to the axes $A_1$, $A_2$, $A_3$, $A_4$ of the peg holes for guiding a drill into the bone fragments at the required orientation. That is, the guide holes together with the peg holes define a drill guide path along the axes with sufficient depth to accurately guide a drill (not shown) to drill holes at the desired pin orientations. The volar plate 102 and guide plate 146 are also preferably provided with mating elements, such as a plurality of holes 156, 158 on the second side of the volar plate (FIG. 2), and a plurality of protuberances 160 on the mating side of the guide plate (FIG. 7), to temporarily stabilize the guide plate on the volar plate during the hole drilling process.

Referring to FIGS. 2 through 9, in use, the volar plate 102 is positioned with its first side 120 against the volar side of the radius. Bone screws 104 (either self-tapping or inserted with the aid of pre-drilled pilot holes) are inserted through the bone screw holes 124, 126, 128 into the radius bone 10 to secure the volar plate 102 to the radius. The bone fragments 16, 18, 20 are then aligned with the radius 10. Next, the guide plate 146 is positioned on the second side of the volar plate. A drill, guided by a guide path formed by the peg holes and the guide holes, drills holes into and between the bone fragments 16, 18, 20 (and possibly also a portion of the integral radius, depending upon the particular location and extent of the fracture), and the guide plate is then removed. The pegs 108 are then inserted through the peg holes 130, 132, 134, 136 and into the holes drilled into the fragments, and the heads of the pegs are threadably engaged in the volar plate. The pegs 108, extending through the oblique-axis peg holes 130, 132, 134, 136, are positioned immediately below the subcondylar bone of the radius and support the bone fragments for proper healing. The volar fixation system thereby secures the bone fragments in their proper orientation.

Figure 10:
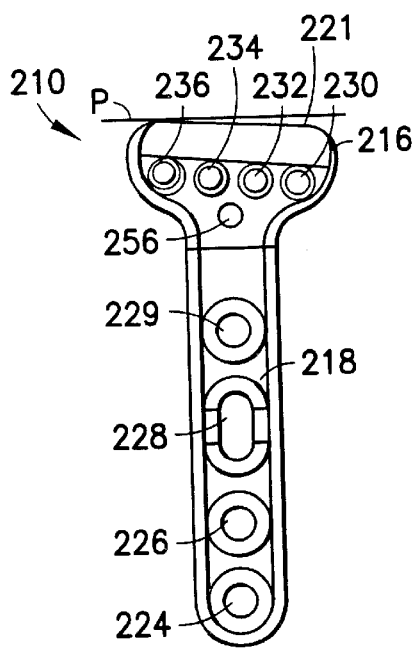
FIG. 10 is a top volar view of a left hand volar fixation system according to the second embodiment of the invention.
Figure 11:
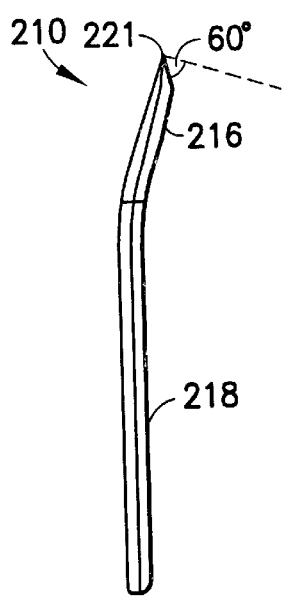
FIG. 11 is a lateral side view of the left hand volar fixation system according to the second embodiment of the invention.
Figure 12:
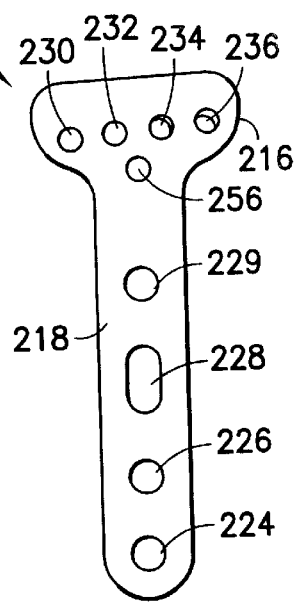
FIG. 12 is a bottom view of the left hand volar fixation system according to the second embodiment of the invention.

Referring to FIGS. 10–12, a second embodiment of a volar plate 210, substantially similar to the first embodiment (with like parts having numbers incremented by 100) and used in substantially the same manner as the first embodiment is shown. The plate 210 preferably has a length of approximately 2.35 inches, which is approximately 0.35 inch greater than in the first embodiment. This additional length accommodates an extra bone screw hole 229 in the body of the volar plate such that the volar plate preferably includes four bone screw holes 224, 226, 228, 229. The additional bone screw in screw hole 229 increases plate stability over the three holes of the first embodiment. The plate 210 preferably tapers in thickness from the body portion 218 to the head portion 216. A preferred taper provides a proximal body portion 218 thickness of approximately 0.098 inch and head portion 216 thickness of approximately 0.078 inch. The taper decreases the thickness of the head portion 216 relative to the body such that the weight of the volar plate is reduced and an improved tendon clearance is provided. The distal edge of the head portion 216 has an increased taper (preferably approximately 60° relative to a line normal to the head) to a distal edge 221. The edge 221 is broken (i.e., made blunt) to prevent irritation or disturbance to the surrounding anatomy.

The head portion 216 includes four threaded peg holes 230, 232, 234, 236 for individually receiving pegs 208 therethrough (FIGS. 13 and 14), and a guide hole 256 for alignment of a guide plate. According to a preferred aspect of the second embodiment of the invention, the peg holes 230, 232, 234, 236, preferably 0.100 inch in diameter, are preferably linearly arranged along the head portion 216, and are provided such that the adjacent peg holes are provided further distally in a medial to lateral direction along the first and second sides. Referring to FIG. 15, more particularly, according to a preferred dimensions of the second embodiment of the invention, the center of peg hole 230 is located approximately 0.321 inch proximal line P and approximately 0.750 inch medial of the lateral edge 237 of the head portion, the center of peg hole 232 is located approximately 0.306 inch proximal line P and 0.557 inch medial of the lateral edge 237, the center of peg hole 234 is located approximately 0.289 inch proximal line P and approximately 0.364 inch medial of the lateral edge 237, and the center of peg hole 236 is located approximately 0.272 inch proximal line P and approximately 0.171 inch medial of the lateral edge 237. As such, the distance from each of the peg holes to the distal edge 221 of the volar plate is relatively greater than in the first embodiment, and provides a preferred alignment with respect to the tapered distal edge 221.

Referring to FIGS. 15–24, in addition, as in the first embodiment, the peg holes define axes $A_1, A_2, A_3, A_4$ which are oblique relative to each other, and more preferably are angled in two dimensions (medial/lateral and proximal/distal) relative to each other; i.e., the pegs 208 once inserted into the peg holes are also angled in two dimensions relative to each other. More particularly, as in the first embodiment, the first axis $A_1$ of the first peg hole 230 is preferably directed normal (FIGS. 16 and 21) to the first side 220 of the head portion 216. The axis $A_2$ of peg hole 232 is preferably angled approximately 1–7° distal (FIG. 17) and approximately 1–7° lateral (FIG. 22) relative to the axis $A_1$, and more preferably approximately 2.5° both distal and lateral relative to axis $A_1$. The axis $A_3$ of peg hole 234 is preferably angled approximately 7–13° distal (FIG. 18) and approximately 7–13° lateral (FIG. 23) relative to axis $A_1$, and more preferably approximately 10° both distal and lateral relative to axis $A_1$. Axis $A_4$ of the peg hole 234 is preferably angled approximately 10–30° distal (FIG. 19) and approximately 10–30° lateral (FIG. 24) relative to axis $A_1$, and more preferably approximately 20° both distal and lateral relative to axis $A_1$.

Referring to FIGS. 13 and 16–19, each of the peg holes has a countersunk portion 270, 272, 274, 276, respectively, for receiving the head 238 of peg 208. Countersunk portions 270, 272 are each preferably approximately 0.030 inch deep and threaded according to the head of the pegs, as described below. Countersunk portion 274 is preferably approximately 0.042 inch deep and likewise threaded. Countersunk portion 276 is preferably approximately 0.056 inch deep and also threaded. The respective depths of the countersunk portions are adapted to better accommodate the heads 238 of the pegs 208 relative to the respective axes of the peg holes.

Figures 13, 14:
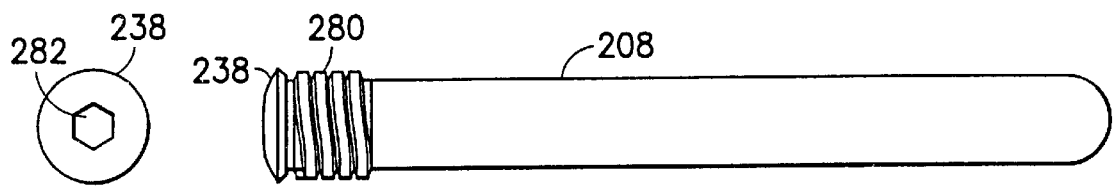
FIG. 13 is an enlarged side elevation of a bone peg according to the second embodiment of the volar fixation system of the invention.
FIG. 14 is a proximal end view of the bone peg of FIG. 13.
Figure 15:
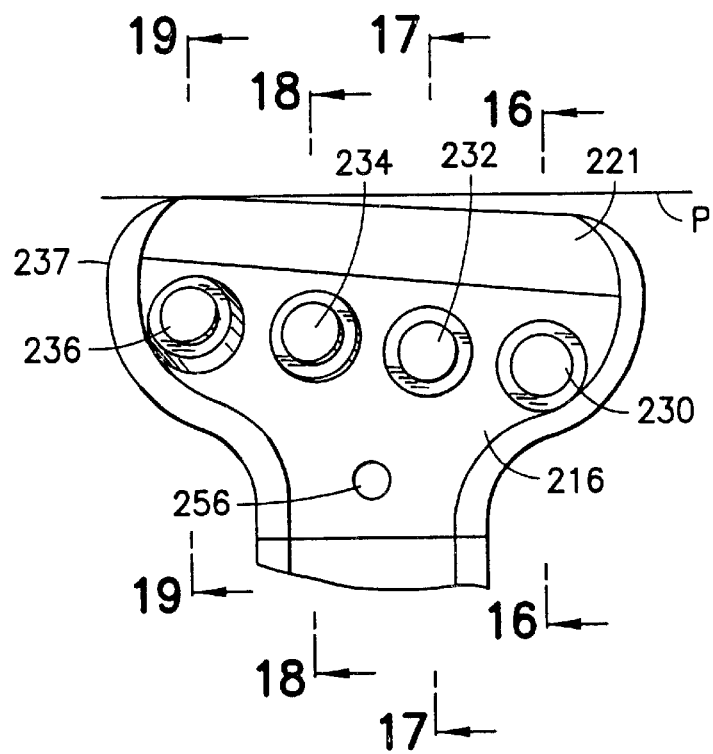
FIG. 15 is first partial top view of the head portion of the left hand volar plate according to the second embodiment of the volar fixation system of the invention.

Referring to FIGS. 13 and 14, the pegs 208, preferably approximately 0.872 inch in length, each have a threaded head 238 adapted to threadably engage threads about the peg holes 230, 232, 234, 236, and have a relatively smooth non-threaded cylindrical shaft 240. The heads 238 preferably include a no. 5 thread 280 at a count of 44 per inch. In addition, the heads 238 are rounded and include a hex socket 282 to facilitate stabilized threading into the peg holes. This design accommodates the reduced thickness of the volar plate at the head portion 216. The shafts 240 are preferably approximately 0.0792 inch (2 mm) in diameter and 0.765 inch in length. Such dimensions permit the pegs to adequately support the bone fragments such that the bone is able to heal correctly. The pegs 208 are also preferably made from titanium alloy, and are preferably 'tiodized' to provide a strong finish which does not adversely affect bone healing.

There have been described and illustrated herein embodiments of a volar fixation system and a method of aligning and stabilizing a Colles' fracture. While particular embodiments of the invention have been described, it is not intended that the invention be limited thereto, as it is intended that the invention be as broad in scope as the art will allow and that the specification be read likewise. Thus, while particular materials for the elements of the system have been disclosed, it will be appreciated that other materials may be used as well. In addition, while a particular numbers of screw holes in the volar plates and bone screws have been described, it will be understood another number of screw holes and screws may be provided. Further, fewer screws than the number of screw holes may be used to secure to the volar plate to the radius. Also, fewer or more peg holes and bone pegs may be used, preferably such that at least two pegs angled in two dimensions relative to each other are provided. Moreover, while in the first embodiment it is preferred that the peg holes lie along a parabolic curve, it will be appreciated that they can lie along another curve. In addition, while a particular preferred angle between the head portion and body portion has been disclosed, other angles can also be used. Furthermore, while particular distances are disclosed between the peg holes and line P, it will be appreciated that the peg holes may be provided at other distances relative thereto. Moreover, while particular preferred medial/lateral and proximal/distal angles for the peg hole axes has been disclosed, it will be appreciated that yet other angles may be used in accord with the invention. Also, while a right-handed volar plate is described with respect to the first embodiment, and a left-handed volar plate is described with respect to the second embodiment, it will be appreciated that each embodiment may be formed in either a right- or left-handed model, with such alternate models being mirror images of the models described. In addition, aspects from each of the embodiments may be combined. It will therefore be appreciated by those skilled in the art that yet other modifications could be made to the provided invention without deviating from its spirit and scope as claimed.

What is claimed is:

1. A volar fixation plate, comprising:
a substantially rigid plate including a distal head portion and a proximal body portion angled relative to said head portion,
said head portion defining a plurality of threaded peg holes adapted to individually receive fixation pegs therein, said peg holes each having a center substantially lying along a parabolic curve, and
said body portion including at least one screw hole.

2. A volar fixation plate according to claim 1, wherein:
said peg holes define a plurality of axes at least two of which are oblique relative to each other.

3. A volar fixation plate according to claim 2, wherein:
each of said at least two axes is oblique in two dimensions relative to another of said at least two axes.

4. A volar fixation plate according to claim 1, wherein:
said head portion defines a medial side and a lateral side, and said peg holes are arranged in a generally medial to lateral direction wherein successive lateral peg holes are situated distally relative to adjacent peg holes.

5. A volar fixation plate according to claim 1, wherein:
said head portion includes exactly four peg holes.

6. A volar fixation plate according to claim 2, wherein:
said head portion includes a lower surface, and a first of said plurality of peg holes defines a first axis of said plurality of axes directed substantially normal to said lower surface,
a second of said plurality of peg holes defines a second axis of said plurality of axes angled approximately 1–7° distal and 1–7° lateral relative to the first axis,
a third of said plurality of peg holes defines a third axis of said plurality of axes angled approximately 7–13° distal and 7–13° lateral relative to the first axis, and
a fourth of said plurality of peg holes defines a fourth axis of said plurality of axes angled approximately 10–30° distal and 10–30° lateral relative to the first axis.

7. A volar fixation plate according to claim 2, wherein:
said head portion includes a lower surface, and a first of said plurality of peg holes defines a first axis of said plurality of axes directed substantially normal to said lower surface,
a second of said plurality of peg holes defines a second axis of said plurality of axes angled approximately 2.5° distal and 2.5° lateral relative to the first axis,
a third of said plurality of peg holes defines a third axis of said plurality of axes angled approximately 10° distal and 10° lateral relative to the first axis, and
a fourth of said plurality of peg holes defines a fourth axis of said plurality of axes angled approximately 20° distal and 20° lateral relative to the first axis.

8. A volar fixation plate, comprising:
a substantially rigid plate including a distal head portion and a proximal body portion angled relative to said head portion,
said head portion defining a plurality of threaded peg holes adapted to individually receive fixation pegs therethrough, said peg holes linearly arranged in a generally medial to lateral direction wherein successive lateral peg holes are situated distally relative to adjacent peg holes, and
said body portion including at least one screw hole.

9. A volar fixation plate according to claim 8, wherein:
said peg holes define a plurality of axes at least two of which are oblique relative to each other.

10. A volar fixation plate according to claim 9, wherein:
each of said at least two axes is oblique in two dimensions relative to another of said at least two axes.

11. A volar fixation plate according to claim 8, wherein:
said head portion includes exactly four peg holes.

12. A volar fixation plate according to claim 9, wherein:
said head portion includes a lower surface, and a first of said plurality of peg holes defines a first axis of said plurality of axes directed substantially normal to said lower surface,
a second of said plurality of peg holes defines a second axis of said plurality of axes angled approximately 1–7° distal and 1–7° lateral relative to the first axis,
a third of said plurality of peg holes defines a third axis of said plurality of axes angled approximately 7–13° distal and 7–13° lateral relative to the first axis, and
a fourth of said plurality of peg holes defines a fourth axis of said plurality of axes angled approximately 10–30° distal and 10–30° lateral relative to the first axis.

13. A volar fixation plate according to claim 9, wherein:
said head portion includes a lower surface, and a first of said plurality of peg holes defines a first axis of said plurality of axes directed substantially normal to said lower surface,
a second of said plurality of peg holes defines a second axis of said plurality of axes angled approximately 2.5° distal and 2.5° lateral relative to the first axis,
a third of said plurality of peg holes defines a third axis of said plurality of axes angled approximately 10° distal and 10° lateral relative to the first axis, and
a fourth of said plurality of peg holes defines a fourth axis of said plurality of axes angled approximately 20° distal and 20° lateral relative to the first axis.

14. A volar fixation plate according to claim 8, wherein:
said head portion is angled approximately 18° relative to said body portion.

15. A volar fixation plate according to claim 8, wherein:
said head portion and said body portion are provided in a substantially T-shaped configuration relative to each other, with said body portion intersecting said head portion.

16. A volar fixation plate, comprising:
a substantially rigid plate including a distal head portion and a proximal body portion,
    said head portion defining a plurality of threaded peg holes adapted to individually receive fixation pegs therein, said plurality of peg holes defining a plurality of axes, a first axis of said plurality of axes directed substantially normal to a lower surface of said head portion,
    a second of said plurality of axes angled approximately 1–7° distal and 1–7° lateral relative to the first axis,
a third axis of said plurality of axes angled approximately 7–13° distal and 7–13° lateral relative to the first axis, and
a fourth axis of said plurality of axes angled approximately 10–30° distal and 10–30° lateral relative to the first axis, and
said body portion including at least one screw hole.

17. A volar fixation plate according to claim 16, wherein:
said second axis is angled approximately 2.5° distal and 2.5° lateral relative to the first axis,
said third axis is angled approximately 10° distal and 10° lateral relative to the first axis, and
said fourth axis is angled approximately 20° distal and 20° lateral relative to the first axis.

18. A volar fixation plate according to claim 16, wherein:
each of said plurality of axes is oblique in two dimensions relative to the other of said plurality of axes.

19. A volar fixation plate according to claim 16, wherein:
said head portion includes exactly four peg holes.

20. A volar fixation plate according to claim 16, wherein:
said head portion defines a medial side and a lateral side, and said peg holes are arranged in a generally medial to lateral direction wherein successive lateral peg holes are situated distally relative to adjacent peg holes.

21. A volar fixation plate according to claim 16, wherein:
said peg holes are linearly arranged.

22. A volar fixation plate according to claim 16, wherein:
said peg holes lie on a curve.

23. A volar fixation plate according to claim 22, wherein:
said curve is a parabolic curve.

24. A volar fixation system, comprising:
a) a substantially rigid plate including a distal head portion and a proximal body portion, said head portion defining a plurality of threaded peg holes defining a plurality of axes at least two of which are oblique relative to each other, and said body portion including at least one screw hole; and
b) a plurality of pegs each having a threaded head portion and a shaft portion, said threaded head portion sized to engage said threaded peg holes and said shaft portion sized to be received through said peg holes such that each of said shaft portions extends along a respective one of said plurality of the axes.

25. A volar fixation system according to claim 24, wherein:
each of said at least two axes is oblique in two dimensions relative to another of said at least two axes.

26. A volar fixation system according to claim 24, wherein:
said head portion of each of said pegs includes a hex socket.

27. A volar fixation system according to claim 24, wherein:
said head portion of each of said pegs includes a rounded head.

28. A volar fixation system according to claim 24, wherein:
said head portion of each of said pegs includes a no. 5 thread.

29. A volar fixation system according to claim 24, wherein:
said shaft portion of each of said pegs is a non-threaded cylinder.

30. A volar fixation system according to claim 24, further comprising:
c) at least one screw adapted to be received in said at least one screw hole.

31. A volar fixation system according to claim 30, wherein:
said at least one screw is a self-tapping screw.

32. A volar fixation system according to claim 24, further comprising:
c) a guide plate adapted to be positioned over at least a portion of said volar plate, said guide plate including a plurality of guide holes, and when said guide plate is positioned over said volar plate, said guide holes and said peg holes together define a drill guide adapted to axially direct a drill therethrough.

33. A volar fixation system according to claim 32, wherein:
said volar plate and said guide plate include mating elements which align said guide plate over said volar plate.

34. A volar fixation system according to claim 24, wherein:
said shaft portion is approximately 0.0675 inch in diameter and approximately 0.76 inch in length.

35. A volar fixation system according to claim 24, wherein:
said head portion of said plate is angled relative to said body portion of said plate.

* * * * *